(12) United States Patent
Trentini et al.

(10) Patent No.: US 11,931,442 B2
(45) Date of Patent: *Mar. 19, 2024

(54) PERSONAL CLEANSING COMPOSITION (71) Applicant: Conopco, Inc., Englewood Cliffs, NJ (US)

(72) Inventors: Massimiliano Trentini, Old Saybrook, CT (US); Helen Diane Thompson, Liverpool (GB); Christopher David Bentley, Liverpool (GB); Lynsey Joanne Coan, Bromborough (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 436 days.

This patent is subject to a terminal disclaimer.

(21) Appl. No.: 16/640,660

(22) PCT Filed: Aug. 22, 2018

(86) PCT No.: PCT/EP2018/072599
§ 371 (c)(1),
(2) Date: Feb. 20, 2020

(87) PCT Pub. No.: WO2019/038308
PCT Pub. Date: Feb. 28, 2019

(65) Prior Publication Data
US 2020/0352838 A1    Nov. 12, 2020

(30) Foreign Application Priority Data
Aug. 25, 2017 (EP) ..................... 17187894

(51) Int. Cl.
*C11D 1/02* (2006.01)
*A61K 8/20* (2006.01)
(Continued)

(52) U.S. Cl.
CPC ............. *A61K 8/42* (2013.01); *A61K 8/20* (2013.01); *A61K 8/442* (2013.01); *A61K 8/466* (2013.01);
(Continued)

(58) Field of Classification Search
CPC .... C11D 1/12; C11D 1/28; C11D 1/40; C11D 1/94; C11D 3/30; C11D 3/32
(Continued)

(56) References Cited

U.S. PATENT DOCUMENTS 4,479,893 A * 10/1984 Hirota ................ A61K 8/556
510/122
4,758,376 A * 7/1988 Hirota ................ A61K 8/37
424/70.11
(Continued)

FOREIGN PATENT DOCUMENTS

CN 104997661 10/2015
JP 2001220325 8/2001
(Continued)

OTHER PUBLICATIONS

Search Report and Written Opinion in PCTEP2018072599; dated Nov. 26, 2018.
(Continued)

*Primary Examiner* — Gregory R Delcotto
(74) *Attorney, Agent, or Firm* — Krista J. Aiello (57) ABSTRACT

Disclosed are water-based personal cleansing compositions having an isotropic surfactant phase, the compositions containing (a) an amidoamine surfactant, (b) cleansing surfactant, (c) water, and (d) protonating agent, the cleansing surfactant containing 85 to 100% by weight of a combination of betaine surfactant and taurate surfactant in particular ratios; also disclosed are methods of thickening such compositions by the addition of electrolyte.

19 Claims, 7 Drawing Sheets

(51) Int. Cl.
  *A61K 8/42* (2006.01)
  *A61K 8/44* (2006.01)
  *A61K 8/46* (2006.01)
  *A61Q 19/10* (2006.01)
  *C11D 1/12* (2006.01)
  *C11D 1/28* (2006.01)
  *C11D 1/40* (2006.01)
  *C11D 1/90* (2006.01)
  *C11D 3/30* (2006.01)
  *C11D 3/32* (2006.01)

(52) U.S. Cl.
  CPC ............... *A61Q 19/10* (2013.01); *C11D 1/12* (2013.01); *C11D 1/28* (2013.01); *C11D 1/40* (2013.01); *C11D 3/30* (2013.01); *C11D 3/32* (2013.01); *A61K 2800/262* (2013.01); *A61K 2800/596* (2013.01)

(58) Field of Classification Search
  USPC ....... 510/123, 126, 130, 137, 138, 477, 488, 510/499, 501, 504
  See application file for complete search history.

(56) References Cited

U.S. PATENT DOCUMENTS

| | | | | |
|---|---|---|---|---|
| 5,137,715 A | * | 8/1992 | Hoshowski | A61K 8/463 424/70.17 |
| 5,393,519 A | * | 2/1995 | Dowell | A61K 8/24 510/119 |
| 5,587,154 A | * | 12/1996 | Dowell | A61K 8/20 424/70.11 |
| 5,665,267 A | * | 9/1997 | Dowell | A61K 8/20 510/123 |
| 5,945,093 A | * | 8/1999 | Duvel | A61K 8/8164 424/70.12 |
| 6,218,346 B1 | | 4/2001 | Sajic et al. | |
| 6,566,313 B1 | * | 5/2003 | Hohenstein | A61K 8/42 510/125 |
| 6,569,825 B1 | | 5/2003 | Pratley | |
| 6,743,760 B1 | * | 6/2004 | Hardy | A61K 8/442 510/119 |
| 2006/0029559 A1 | * | 2/2006 | Tamura | A61K 8/894 424/70.12 |
| 2011/0165105 A1 | * | 7/2011 | Molenda | A61K 8/33 424/70.9 |
| 2014/0086864 A1 | | 3/2014 | Ishimori et al. | |
| 2015/0238402 A1 | | 8/2015 | Casugbo et al. | |
| 2015/0157540 A1 | | 11/2015 | Rizk et al. | |
| 2015/0157548 A1 | | 11/2015 | De Feij et al. | |
| 2016/0355764 A1 | * | 12/2016 | Joliff | C11D 3/1293 |

FOREIGN PATENT DOCUMENTS

| | | |
|---|---|---|
| WO | WO9932079 | 7/1999 |
| WO | WO2013150301 | 10/2013 |

OTHER PUBLICATIONS

Search Report and Written Opinion in EP17187894; dated Jan. 2, 2018.
IPRP1 in PCTEP2018072599; Feb. 25, 2020.
Search Report and Written Opinion in EP17187893; dated Jan. 2, 2018.
Search Report and Written Opinion in PCTEP2018072600; dated Nov. 26, 2018.
IPRP1 in PCTEP2018072600; Feb. 25, 2020.
Co-pending Application, U.S. Appl. No. 16/640,824.

* cited by examiner

PERSONAL CLEANSING COMPOSITION

CROSS REFERENCE TO RELATED APPLICATIONS

The present application is a U.S. National Phase Application under 35 U.S.C. § 371 of International Application No. PCT/EP2018/072599, filed on Aug. 22, 2018, which claims priority to European Patent Application No. 17187894.5, filed on Aug. 25, 2017, the contents of which are incorporated herein in their entireties.

FIELD OF THE INVENTION

The subject invention relates to personal cleansing compositions, in particular, to water-based personal cleansing compositions including, for example, body washes, facial washes, and shampoos.

BACKGROUND OF THE INVENTION

The selection, amount and relative amount of cleansing surfactant contributes to the microstructure of a personal cleansing composition. In turn, microstructure can impact rheological properties such as composition viscosity and viscosity building characteristics, and may also contribute to composition stability.

A sufficient level of cleansing surfactant is ordinarily needed for surfactant molecules to be able to assemble into micelles, and for the micelles to aggregate to build structure. Commercially available water-based cleansing compositions frequently contain upwards of 12 weight percent of cleansing surfactant. The major cleansing surfactant component of such compositions is commonly an alkyl and/or alkyl ether sulfate surfactant, with lauryl and laureth sulfates, surfactants known to afford good detergency, being among the sulfate surfactants commonly employed. Sulfate surfactants belong to a class of materials known as anionic surfactants. The sulfate surfactants are frequently used together with an amphoteric co-surfactant, with betaine surfactants such as cocamidopropyl betaine and cocamido betaine being among the amphoteric surfactants commonly employed. Betaine surfactants help to boast lather and are generally milder than sulfate surfactants, albeit without the detergent power of the sulfate surfactants. Advantageously, personal cleansing compositions based on sulfate surfactant can normally be thickened by the addition of simple salts.

Despite the widespread use of sulfate surfactants in personal cleansing compositions, there is considerable interest in milder alternatives, including compositions in which the anionic surfactant is or includes a taurate surfactant.

U.S. Pat. No. 6,569,825 discloses aqueous cleansing compositions which include (a) a short-chain anionic surfactant chosen from $C_6$-$C_9$ alkyl ether sulphates, $C_8$-$C_{11}$ acyl lactylates, $C_6$-$C_9$ acyl methyl taurates, $C_6$-$C_9$ acyl isothionates, $C_6$-$C_{11}$ fatty acid soaps, $C_6$-$C_9$ alkyl sulfates, $C_6$-$C_{11}$ acyl sarcosinates, $C_6$-$C_9$ alkyl sulphosuccinates, $C_6$-$C_9$ alkyl ether sulphosuccinates, or mixtures thereof; (b) a long chain anionic surfactant chosen from $C_{13}$-$C_{18}$ alkyl ether sulphates, $C_{13}$-$C_{18}$ acyl lactylates, $C_{13}$-$C_{16}$ acyl methyl taurates, $C_{13}$-$C_{15}$ acyl isothionates, $C_{13}$-$C_{16}$ alkyl sulfates, $C_{13}$-$C_{16}$ acyl sarcosinates, $C_{13}$-$C_{16}$ alkyl sulphosuccinates, $C_{13}$-$C_{16}$ alkyl ether sulphosuccinates, or mixtures thereof; (c) optionally, a medium chain anionic surfactant chosen from $C_{10}$-$C_{12}$ alkyl ether sulphates, $C_{12}$ acyl lactylates, $C_{10}$-$C_{12}$ acyl methyl taurates, $C_{10}$-$C_{12}$ acyl isothionates, $C_{10}$-$C_{12}$ alkyl sulfates, $C_{12}$ acyl sarcosinates, $C_{10}$-$C_{12}$ alkyl sulphosuccinates, $C_{10}$-$C_{12}$ alkyl ether sulphosuccinates, or mixtures thereof, and (d) water; wherein (i) at least one of the surfactants (a) and (b) is selected from the group consisting of the acyl lactylates, the acyl sarcossinates, or the short-chain anioinic surfactant (a) is a $C_9$ to $C_{11}$ fatty acid soap; (ii) if surfactant (c) is present, then the surfactants (a), (b) and (c) are present in an amount such that the weight ratio of (c): [(a)+(b)] is less than 1:1. Among the examples and comparative examples therein disclosed are: Comparative Example F, said to contain 10% cocoether sulphate (3EO)+ 5% cocoamidobetaine; Comparative Example G said to contain 10% $C_8$ taurate+5% cocoamidobetaine; and Example 3, said to contain 7% coco ether sulphate (3EO)+ 3% $C_8$ Taurate+5% cocoamido betaine. In commenting on foam and Zion test data for these compositions, Zion test data therein said to be an indication of composition mildness, the patent reports that the addition of the $C_8$ taurate in the blend of Example 3 boosted lather without adversely affecting mildness. Comparative Example F, Comparative Example G and Example 3 were reported to have foam volumes of 79 ml, 44 ml and 145 ml, respectively.

CN 104997661 discloses what are therein said to be mild, silicone-free shampoos having ingredients that include acrylates/steareth-20 methacrylate copolymer, cocamidopropyl betaine, polyquaternium-10, disodium lauroamphoacetate, methyl cocoyl taurate, behenyl trimethyl ammonium chloride, stearyl amidopropyl dimethylamine, glycol distearate, quaternium-27, and cationic conditioning agents, in amounts as therein more particularly described, including compositions having the following ingredient contents: acrylates/steareth-20 methacrylate copolymer 1~6 percent, cocamidopropyl betaine 20~40 percent, polyquaternium-10 0.25~1.25 percent, disodium lauroamphoacetate 2.5~15 percent, methyl cocoyl taurate 1.0~5 percent, behenyl trimethyl ammonium chloride 0.5~3 percent, stearyl amidopropyl dimethyl amine 0.5~3 percent, glycol distearate 1~3 percent, quaternium-27 0.5~3 percent, and cationic conditioning agents 1~4 percent. The composition is said to be free from sulfate surfactants.

WO 99/32079 discloses shampoo compositions that include a silicone microemulsion, at least one surfactant which is a cationic derivative of guar gum, and a deposition polymer. At page 9, line 28 to page 10, line 4, the patent publication states: "exceptional optical clarity and stability, across a wide range of temperatures, can be achieved with the following combination of cleansing surfactants in the stated amounts: from 4 to 8% by weight of the total shampoo composition of acyl methyl taurate and/or acylated collagen polypeptide; and up to 8% by weight of the total shampoo composition of cocamidopropyl betaine."

US 2014/086864 discloses shampoo compositions comprising a taurine derivative surfactant, an amphoteric surfactant which is an alkylamide betaine, a cationic conditioning polymer, a quaternary ammonium group-containing betaine surfactant, and a quaternary ammonium group-containing silylated urethane polymer. With respect to use on dyed hair, the compositions are therein said to be excellent in fading-inhibiting effect and what is said to be in "in use feeling". The Examples include compositions that, in addition to other ingredients, contain coconut oil fatty acid methyltaurine and coconut oil fatty acid amide propyl betaine in a combined amount of from 6 to 24 mass %.

JP 2001-220325 A2 discloses hair shampoo compositions having a combination of acyl taurate and betaine surfactants. The compositions further include an alkylbis(dihydroxypropyl)amine represented by the formula: $R^7N(CH_2CH(OH)CH_2OH)_2$, where $R^7$ is an alkyl or alkenyl group having 8 to 22 carbons.

Achieving an acceptable composition viscosity is an important factor in providing a mild personal cleansing composition that can be applied in a controlled manner and readily spread in use. Composition viscosity, together with attributes such as foamability can also impact consumer perception of such products. When sulfate surfactants are eliminated or the level thereof significantly reduced, developing a microstructure that results in desirable rheological properties can be challenging, particularly in the case of mild compositions with low cleansing surfactant contents; additionally, building the viscosity of such compositions by the addition of a simple salt can be problematic. Reducing or eliminating sulfate surfactants can also be problematic in regard to formulating mild cleansing compositions that are stable at acidic pHs.

One approach to the issue of thickening systems that are free or essentially free of sulfate surfactants has been to use sulfate-free surfactants together with polymeric thickeners. Polymeric thickeners can have a gelation effect that transforms a product with what is ordinarily Newtonian rheology under conditions of low shear, such as is experienced, for example, during dosing, application and spreading in-use, to a non-Newtonian rheology. In addition to being detectable by a consumer as an undesirable departure from product norms, the use of such thickeners can further limit the ability to subsequently adjust composition viscosity through the use of simple salts.

Employing relatively high levels of non-sulfate surfactant may also assist in building the viscosity of systems that are free or essentially free of sulfate surfactants. The levels of non-sulfate surfactant needed may, however, be higher than conventional norms, and may also result in non-isotropic surfactant systems having relatively non-labile liquid crystalline structures or domains. In contrast to isotropic surfactant systems, the relatively labile microstructure of which tends to promote foaming efficiency, liquid crystalline microstructures tend to "trap" surfactant and impair foamability. Additionally, liquid crystalline structures or domains may impede light transmission and may impart a turbid or cloudy appearance to a composition, which may be problematic where translucency is desired.

One aspect of this invention is to provide mild personal cleansing compositions having desirable rheological properties, including compositions with relatively low surfactant contents. Another aspect of this invention is to provide mild personal cleansing compositions having an isotropic surfactant phase, including compositions that are stable at acidic pHs. Yet another aspect of this invention is to provide mild personal cleansing compositions, including low surfactant content compositions free or essentially free of sulfate surfactants, the viscosity of which compositions may be increased through the addition of electrolytes such as simple salts. Yet another aspect of this invention is to provide mild personal cleansing compositions having a translucent or transparent appearance.

One or more aspects of this invention may be achieved by the compositions and methods hereinafter described.

SUMMARY OF THE INVENTION

Pursuant to the subject invention it was found that inclusion of an amidoamine surfactant in a personal cleansing composition that contains a combination of taurate surfactant, preferably acyl taurate surfactant, and betaine surfactant can further the development and/or strength of the surfactant phase, even at a relatively low cleansing surfactant concentration, and may allow for the further thickening of the compositions by the addition of an electrolyte such as a simple salt.

In one embodiment there is provided a personal cleansing composition comprising:
a) an amidoamine surfactant of the formula:

$$R^5R^6N-(CH_2)_x-NHC(O)R^7 \qquad (I)$$

wherein $R^5$ and $R^6$ are independently methyl or ethyl, x is 2 or 3, and $R^7$ is C6 to C30 alkyl and wherein $R^7$ is saturated or unsaturated,
b) from 5 to 15% weight of cleansing surfactant,
c) water, and
d) protonating agent, wherein the cleansing surfactant contains from 85 to 100% by weight, based on the total weight of the cleansing surfactant, of a combination of betaine surfactant and taurate surfactant and wherein:
when the composition contains 5 to 6 weight percent of cleansing surfactant, the weight ratio of betaine surfactant to taurate surfactant is from 55:45 to 45:55;
when composition contains from greater than 6 weight percent to up to 10 weight percent of cleansing surfactant, the weight ratio of betaine surfactant to taurate surfactant is from 80:20: to 40:60; and
when the composition contains greater than 10 weight percent of cleansing surfactant, the weight ratio of betaine surfactant to taurate surfactant is from 80:20: to 20:80.

Preferably the composition has an isotropic surfactant phase.

According to another embodiment of this invention there is provided a method of adjusting the viscosity of a composition, the method comprising the steps of
I) providing a personal cleansing composition comprising:
a) an amidoamine surfactant of the formula:

$$R^5R^6N-(CH_2)_x-NHC(O)R^7 \qquad (I)$$

wherein $R^5$ and $R^6$ are independently methyl or ethyl, x is 2 or 3, and $R^7$ is C6 to C30 alkyl, and wherein $R^7$ is saturated or unsaturated,
b) from 5 to 15% by weight of cleansing surfactant
water, and
c) protonating agent,
wherein the cleansing surfactant contains from 85 to 100% by weight of a combination of betaine surfactant and taurate surfactant and wherein:
when the composition contains 5 to 6 weight percent of cleansing surfactant, the weight ratio of betaine surfactant to taurate surfactant is from 55:45 to 45:55;
when composition contains from greater than 6 weight percent to up to 10 weight percent of cleansing surfactant, the weight ratio of betaine surfactant to taurate surfactant is from 80:20: to 40:60; and
when the composition contains greater than 10 weight percent of cleansing surfactant, the weight ratio of betaine surfactant to taurate surfactant is from 80:20: to 20:80; and
II) adding electrolyte to the composition,
wherein the addition of electrolyte increases the viscosity of the composition.

DETAILED DESCRIPTION OF THE INVENTION

Unless indicated otherwise, as used herein, "%" means weight %, alternatively referred to as % by weight. All references to the amount by weight of a component of the instant composition are, unless indicated otherwise, based on the total weight of the composition. Unless indicated otherwise, all ratios are by weight. Unless indicated to the contrary, reference to the amount of a composition component is to the amount of component as active.

All numerical ranges employed in this description ought to be understood as modified by the word "about". Numerical ranges are understood to encompass the ranges expressly disclosed, as well as ranges subsumed by same. Where the system or method of the subject invention is described as "including" or "comprising" specific components and/or features, narrower embodiments that "consist essentially of" or "consist of" the recited components and/or features are also contemplated.

Amidoamine Surfactant

The amidoamine surfactant suitable for use herein are represented by the formula:

$$R^5R^6N\text{—}(CH_2)_x\text{—}NHC(O)R^7 \quad (I)$$

wherein $R^5$ and $R^6$ are independently methyl or ethyl, x is 2 or 3, and $R^7$ is C6 to C30 alkyl, wherein $R^7$ is saturated or unsaturated. In one embodiment, $R^7$ is C6 to C24 alkyl. In one embodiment, $R^5$ and $R^6$ are methyl and x is 3. Examples of such amidoamines are stearamidopropyldimethylamine, stearamidoethyldiethylamine, stearamidopropyldiethylamine, palmitoamidopropyldimethylamine, palmitamidopropyldiethylamine, palmitoamidoethyldimethylamine, behenamidopropyldimethylamine, behenamidoethyldimethylamine, and arachiamidopropyldimethylamine. One particularly useful amidoamine is stearamidopropyldimethylamine.

Without wishing to be bound by theory, it is believed that in the presence of a protonating agent such as, for example, an organic or mineral acid, the amidoamine may form what is, in effect, a non-permanent quaternary ammonium or pseudo-quaternary ammonium cationic surfactant. Examples of acids suitable for use as protonating agents include, for example, hydrochloric acid, acetic acid, tartaric acid, lactic acid, malic acid and citric acid.

In one embodiment, the personal cleansing composition of the subject invention contains a total amount of up to 2 wt. % of the amidoamine surfactant, based on the total weight of the composition. In another embodiment the composition contains up to 1.5 wt. % of the amidoamine surfactant, based on the total weight of the composition. In yet another embodiment, the personal cleansing composition contains from 0.05 to 1 wt. % of the amidoamine surfactant, based on the total weight of the composition. In yet another embodiment the personal cleansing composition contains from 0.1 to 0.5 wt % of the amidoamine surfactant, based on the total weight of the composition. In yet another embodiment, the personal cleansing composition contains from 0.1 to 0.3 wt. % of the amidoamine surfactant, based on the total weight of the composition.

Cleansing Surfactant

As used herein the term "cleansing surfactant" refers to anionic and amphoteric/zwitterionic surfactants; cationic surfactant, including the amidoamine surfactant, and nonionic surfactant are not considered to be part of the cleansing surfactant. The cleansing surfactant of the instant invention includes both taurate surfactant and betaine surfactant. In one embodiment, cleansing surfactant is present in an amount of from 5 to 15 wt. %, based on the total weight of the personal cleansing composition. In another embodiment, cleansing surfactant is present in an amount of from 6 to 12 wt. %, based on the total weight of the personal cleansing composition. In yet another embodiment, cleansing surfactant is present in an amount of from 6 to 10 wt. %, based on the total weight of the personal cleansing composition. In yet another embodiment, cleansing surfactant is present in an amount of from 8 to 10 wt. %, based on the total weight of the personal cleansing composition.

Taurate Surfactant

Included among the taurate surfactants employed herein are acylamides of taurine or N-methyltaurine, and salts thereof, for example, acyl taurates represented by the general formula:

$$R^8C(O)N(R^9)(CH_2)_y\text{SO}_3M \quad (IIa),$$

and preferably by the general formula

$$R^8C(O)N(R^9)CH_2CH_2SO_3M \quad (IIb),$$

where $R^8$ is C6 to C30, more particularly C6 to C24 alkyl, y is 2 or 3, $R^9$ is hydrogen or methyl, and M is a solubilizing cation such as, for example, hydrogen, ammonium, alkali metal cation, a lower, i.e., C to C4, alkanolammonium cation, or a basic amino acid cation. In one embodiment, $R^8$ is C8 to C18 alkyl. In one embodiment at least half of the $R^8$ groups are C8-C18 alkyl. In another embodiment at least half of the $R^8$ groups are C10 to C14 alkyl. $R^8$ may be saturated or unsaturated. In one embodiment $R^9$ is methyl.

Suitable acyl taurates according to formula IIa include, for example, taurates commonly known as sodium methyl lauroyl taurate, potassium methyl lauroyl taurate, sodium methyl myristoyl taurate, potassium methyl myristoyl taurate, ammonium methyl myristoyl taurate, sodium methyl cocoyl taurate, potassium methyl cocoyl taurate, ammonium methyl cocoyl taurate, sodium methyl oleoyl taurate, potassium methyl oleoyl taurate, ammonium methyl oleoyl taurate, sodium lauroyl taurate, potassium lauroyl taurate, ammonium myristoyl taurante, sodium cocoyl taurate, potassium oleoyl taurate, and the like. In one embodiment, a salt of the coconut fatty acid amide of N-methyltaurine is of particular interest.

Betaine Surfactant

Among the suitable betaines for use herein are betaines represented by the general formula:

$$R^{10}[C(O)NH\text{—}(CH_2)_y]_z\text{—}N^+(R^{11})(R^{12})CH_2CO_2^- \quad (III)$$

where $R^{10}$ is C6 to C30, more particularly C6 to C24 alkyl, z is 0 or 1, $R^{11}$ and $R^{12}$ are independently alkyl, hydroxyalkyl or carboxyalkyl of 1 to 3 carbon atoms, and y is 2 or 3; and salts thereof. In one embodiment, at half of the groups $R^{10}$ are C8 to C18 alkyl. In another embodiment, at least half of the groups $R^{10}$ are C10 to C14 alkyl. $R^{10}$ may be saturated or unsaturated. In one embodiment, $R^{10}$ is derived from coconut oil or palm kernel oil. In one embodiment $R^{11}$ and $R^{12}$ are methyl.

The formula (III) betaines include the simple betaines:

$$R^{10}-N^+(R^{11})(R^{12})CH_2CO_2^-  \quad (IIIa)$$

where $R^{10}$, $R^{11}$, and $R^{12}$ are as described above, and the amidobetaines:

$$R^{10}C(O)NH-(CH_2)_y-N^+(R^{11})(R^{12})CH_2CO_3^-  \quad (IIIb)$$

where $R^{10}$, $R^{11}$, $R^{12}$, and y are as described above.

In one embodiment the betaine surfactant is an amidobetaine, preferably cocamidopropylbetaine.

While the inclusion of cleansing surfactant in addition to the taurate surfactant and betaine surfactants is contemplated, such additional cleansing surfactant, when present, is a minor component of the total cleansing surfactant. In one embodiment the cleansing surfactant contains from 85 to 100% by weight, based on the total weight of the personal cleansing composition, of a combination of betaine surfactant and taurate surfactant. In another embodiment the cleansing surfactant contains from 90 to 100% by weight, based on the total weight of the personal cleansing composition, of a combination of betaine surfactant and taurate surfactant. In another embodiment the cleansing surfactant contains from 95 to 100% by weight, based on the total weight of the personal cleansing composition, of a combination of betaine surfactant and taurate surfactant. In yet another embodiment the cleansing surfactant contains from 99 to 100% by weight, based on the total weight of the personal cleansing composition, of a combination of betaine surfactant and taurate surfactant.

The personal cleansing composition is free or essentially free of sulfate surfactant. "Essentially free of sulfate surfactant" means that the amount of sulfate surfactant, if present, does not exceed 0.5% by weight of the composition. In one embodiment the composition is free or essentially free of additional anionic surfactant. "Essentially free of additional anionic surfactant" means that the amount of anionic surfactant in addition to the taurate surfactant does not exceed 0.5% by weight of the composition.

In one embodiment, when the personal cleansing composition contains 5 to 6 weight percent or less of cleansing surfactant, the weight ratio of betaine surfactant to taurate surfactant is from 55:45 to 45:55, preferably from 50:50 to 45:55. In one embodiment, when the composition contains from greater than 6 weight percent to up to 10 weight percent of cleansing surfactant, the weight ratio of betaine surfactant to taurate surfactant is from 80:20 to 40:60, preferably from 75:25 to 50:50. In one embodiment, when the composition contains from greater than 10 weight percent to up to 15 weight percent of cleansing surfactant, the weight ratio of betaine surfactant to taurate surfactant is from 80:20: to 20:80, preferably from 75:25 to 25:75.

Water

Water is also included in the personal cleansing compositions of the present invention. Water is generally present in a total amount of from 70 to 95%. by weight. In one embodiment, water is present in a total amount of from 75 to 95% by weight. In another embodiment, water is present in a total amount of from 85 to 93% by weight. In yet another embodiment, water is present in a total amount of from 85 to 90% by weight.

Electrolyte

The personal cleansing compositions of the invention may further comprise electrolyte. The addition of electrolyte may assist in adjusting composition viscosity. Electrolytes are materials that dissolve in water and ionize. The term excludes materials such as cleansing surfactant, amidoamine- and other cationic surfactants, as well as other materials that aggregate in solution. Among the electrolytes suitable for use herein are simple salts of organic or inorganic acids. Chlorides, nitrates, sulfates, and carboxylates are among the suitable salts. Examples of suitable electrolytes are sodium chloride, ammonium chloride, magnesium chloride, sodium sulfate and sodium citrate. Typically the electrolytes are relatively small molecules that frequently have nominal molecular weights of less than 600 g/mol.

When present, the total amount of electrolyte is preferably less than 5 wt. %, more preferably less than 4 wt. % based on the total weight of the personal cleansing composition. In one embodiment electrolyte is present in an amount of from 0.05 to 3 wt. %, based on the total weight of the personal cleansing composition. In another embodiment, electrolyte is present in an amount of from 0.1 to 2 wt. %, based on the total weight of the personal cleansing composition. In yet another embodiment, electrolyte is present in an amount of from 0.1 to 1.5 wt. % In still another embodiment, electrolyte is present in an amount of from 0.1 to 1 wt. %, based on the total weight of the personal cleansing composition.

While the addition of electrolyte may assist in building composition viscosity, at too high a level, it may detract from the translucency of the composition. Where translucency is or transparency is desired, the amount of cleansing surfactant and relative amount of betaine surfactant to taurate surfactant should be selected such that little or no added electrolyte is needed to build viscosity, while at the same time keeping the amount of cleansing surfactant at a level where such surfactant does not undesirably impact transmission of light through the composition. In this regard, a total cleansing surfactant content of from 6 to 10 weight may be of particular interest.

Light transmission Light transmission through a composition is conveniently measured using a Formulaction Turbiscan LAB, which uses a Static Multiple Light Scattering method. Applying such measurement technique, a ΔT of >-20% (compared against a sample of distilled water) is herein considered to be "transparent".

Excluding products in pre-diluted form or products formulated as relatively non-viscous or "water thin" products for applicators such as, for example, pump foamers, the personal cleansing compositions of the subject invention have or are adjusted to viscosities in the range of from 2500 cP to 10000 cP, depending upon the particular product form of the composition, and the desired thickness thereof. In one embodiment viscosities in a range of from 3000 to 9000 cP are of interest. In yet another embodiment viscosities in a range of from 3500-8000 cP are of interest. In yet another embodiment viscosities in a range of from 4000-6000 cP are of interest. Unless otherwise indicated, viscosity references are given with respect to measurements obtained using an AR2000EX rheometer from TA Instruments (30° C., 1 mm gap, 90 sec equilibrium time, 30 sec measurement, at 4 reciprocal seconds, 40 mm steel plate spindle).

The personal cleansing compositions of the subject invention are commonly formulated to an acidic pH. In one embodiment, the compositions are formulated to a pH of from 3.5 to less than 7.0. In another embodiment, compositions formulated to pH of from 4 to 6 are of interest. In yet another embodiment, compositions formulated to a pH of from 4 to 5.5 are of interest. In yet another embodiment the composition has a pH of from 4 to 5.

Additional Optional Ingredients

The personal cleansing compositions of the invention may contain one or more additional ingredients for enhancing performance and/or consumer appeal. Such ingredients include, for example, fragrance, fragrance encapsulates, botanical extracts, fruit extracts, and other emotives, dyes, pigments, pH adjusting agents, buffers, pearlescers, opacifiers, preservatives, humectants, suspending agents, skin and/or hair conditioners, skin and/or hair nutrients, vitamins, amino acids, preservatives, and bactericides, to name a few. In one embodiment, the total amount of such additional optional ingredients is less than 15 wt % of the personal cleansing composition. In another embodiment, the total amount of such additional optional ingredients is less than 10 wt % of the personal cleansing composition. In yet another embodiment, the total amount of such additional optional ingredients is from 0.01 to 5 wt % of the personal cleansing composition. The amount of additional optional ingredients will depend, in part, upon the particular ingredient, the use for which it is employed, and the properties desired from its use.

In one embodiment the personal cleansing composition is free or essentially free of (meth)acrylate polymers and copolymers. "Essentially free of (meth)acrylate polymers or copolymers" means that the total amount of such polymers and copolymers, if present, does not exceed 0.0.01 wt. % of the personal cleansing composition. In one embodiment, the personal cleansing composition is free or essentially free of quaternary ammonium group-containing silylated urethane polymer. "Essentially free of quaternary ammonium group-containing silylated urethane polymer" means that the total amount of such polymer, if present, is less than 0.01 wt. % of the personal cleansing composition. In one embodiment the personal cleansing composition is free or essentially free of a cationic derivative of guar gum. "Essentially free of a cationic derivative of guar gum" means that, if present, the total amount thereof is less than 0.01 wt. % of the composition.

The personal cleansing compositions may be prepared by conventional techniques wherein the amidoamine surfactant and cleansing surfactant are solubilized in water, typically with heating and stirring, and cooled, as needed, to a temperature that allows for subsequent addition of other composition ingredients. Cooling and subsequent ingredient addition may be staged, based on the properties of the ingredients subsequently added. For example fragrance and other volatile components are typically added when the composition is below a temperature at which they volatize. Heated surfactant solutions in which the amidoamine surfactant is solubilized should not be cooled so rapidly as to precipitate same.

The personal cleansing compositions of this invention may be provided in a variety of product forms including, for example, body washes, facial washes and shampoos. In one embodiment, compositions in the form of shampoos are of particular interest. The personal cleansing composition is typically diluted with water and worked into a lather. Unless expressly indicated otherwise, the percentages of composition ingredients recited herein are with reference to the composition prior to dilution in use, that is, in the composition as packaged. The personal cleansing compositions may be provided in packaging that includes directions that convey that the composition is to be applied, lathered and rinsed-Off.

EXAMPLES

In the Examples that follow, stearamidopropyl dimethyl amine is alternatively referred to as "TAS", cocamidopropyl betaine is alternatively referred to as "CAPB" or "Betaine", and sodium cocoyl taurate is alternatively referred to as "Taurate". In the tables that follow the reported wt. % of listed ingredients is given in reference to such ingredients as separately added components. For example, the reported wt. % of disodium EDTA, sodium chloride and sodium benzoate does not take into account such materials, if any, included as part of any ingredients identified in the Tables by brand name. Compositions as described in Tables 1, 2A and 3 below were prepared by means of the following general procedure:

Heat an initial aliquot of water (deionized) to a target temperature of 63° C. to 65° C.; if used, add the stearamidopropyl dimethyl amine and mix until dissolved. Discontinue heating, add the sodium cocoyl taurate (Pureact WS Conc) and mix until dissolved; add the cocamidopropyl betaine (Tego® Betain CK KB5) and mix for approximately 5 minutes. When the mixture has cooled to 40° C. to 43° C., add the additional water (deionized), into which is mixed the polyquaternium-10. Then add the disodium EDTA, sodium benzoate, fragrance and citric acid and mix for 10 minutes.

Example 1

The general procedure above was used to prepare a series of samples as described in Table 1 (6 compositions per sample series; TAS present in an amount of 0 (no TAS), 0.1, 0.2, 0.3, 0.4 or 0.5 wt. %).

TABLE 1

| | Sample Series | | | | | |
|---|---|---|---|---|---|---|
| Ingredient wt. % | A | B | C | D | E | F |
| Initial Aliquot of Water | To 100 | To 100 | To 100 | To 100 | To 100 | To 100 |
| Additional Water | 12.0 | 12.0 | 12.0 | 12.0 | 12.0 | 12.0 |
| Polyquaternium-10 | 0.2 | 0.2 | 0.2 | 0.2 | 0.2 | 0.2 |
| Tego ® Betain CK KB5* | 3.33 | 6.66 | 10.00 | 6.87 | 13.75 | 20.63 |
| Pureact WS Conc.** | 10.00 | 6.66 | 3.33 | 20.63 | 13.75 | 6.87 |
| Stearamidopropyl dimethyl amine (TAS) | 0 to 0.5 | 0 to 0.5 | 0 to 0.5 | 0 to 0.5 | 0 to 0.5 | 0 to 0.5 |
| Fragrance | 0.9 | 0.9 | 0.9 | 0.9 | 0.9 | 0.9 |
| Disodium EDTA | 0.05 | 0.05 | 0.05 | 0.05 | 0.05 | 0.05 |
| Sodium Benzoate | 0.45 | 0.47 | 0.45 | 0.47 | 0.43 | 0.40 |
| Citric Acid (50 wt. % aqueous solution) | 1.2 | 1.2 | 1.2 | 1.2 | 1.2 | 1.2 |
| Total Cleansing surfactant (wt. %) | 4 | 4 | 4 | 8.25 | 8.25 | 8.25 |

TABLE 1-continued

| Ingredient wt. % | Sample Series | | | | | |
|---|---|---|---|---|---|---|
| | A | B | C | D | E | F |
| Wt. Ratio Betaine:Taurate | 25:75 | 50:50 | 75:25 | 25:75 | 50:50 | 75:25 |

*Tego ® Betain CK KB5 from Evonik Industries; ≈30% cocamidopropyl betaine
**Pureact WS CONC from Innospec Performance Chemicals; ≈30% sodium methyl cocoyl taurate Viscoelastic properties of the compositions under harmonic oscillation were obtained employing a TA ARES-G2 rheometer with 50 mm parallel plate geometry (1 mm gap). Measurements were made at 25° C. A frequency range of 0.01 to 100 Hz was applied to the compositions at 1% strain, with the elastic modulus (G') and loss modulus (G") of the composition being measured as a function of frequency. An isotropic surfactant phase is a surfactant phase in which the predominant surfactant microstructures are micelles of aggregated surfactant molecules. Preferably the surfactant phase is an isotropic, rod-like micellar system, that is, a system in which the predominant surfactant microstructure is that of generally rod-like micelles. For an isotropic, rod-like micellar system, the oscillatory response resembles a Maxwell spring and dashpot model where, below the crossover frequency (crossover frequency representing the frequency where G'=G"), the ratio of the slope of G' to the slope of G" is approximately 2 to 1.

Figure 1:
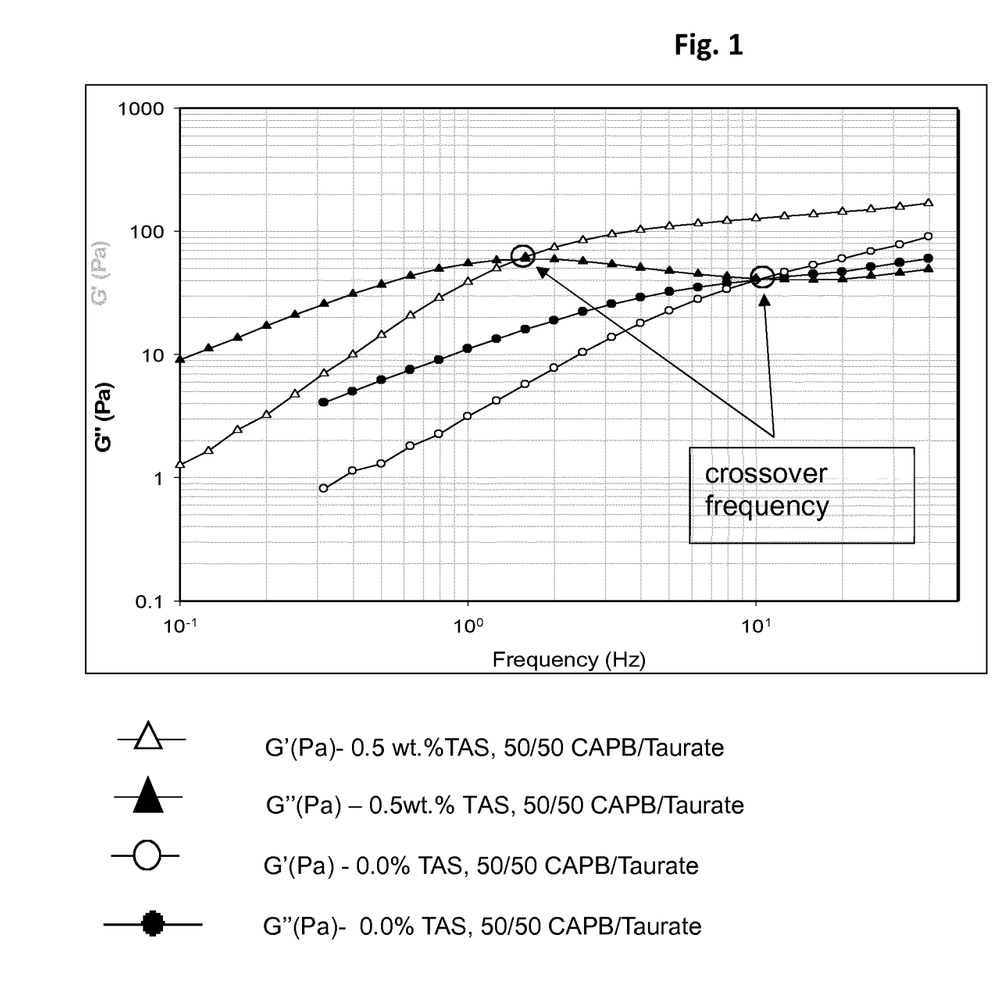
FIG. 1 is a graph showing the shift in crossover frequency under dynamic oscillation that occurs with the addition of stearamidopropyl dimethylamine to a composition having a combined content of taurate surfactant and betaine surfactant of 8.25 wt. % and a weight ratio of betaine surfactant to taurate surfactant of 50:50.

FIG. 1 is a graph comparing the elastic modulus (G') and elastic loss modulus (G") of compositions from the Sample E series (combined content of taurate and betaine of 8.25 wt. %; weight ratio of betaine:taurate of 50:50) at stearamidopropyl dimethylamine levels of 0 or 0.5 wt. %. The graph shows the shift in crossover frequency that occurs by the addition of stearamidopropyl dimethylamine, demonstrating the addition of stearamidopropyl dimethylamine to be effective in building micellar structure of the composition. The ratio of the slope of G' to the slope of G" below the crossover of G' and G" is approximately 2 to 1, indicative of the composition having an isotropic, rod-like micellar system.

The reciprocal of the frequency at the crossover of G' and G", where G'=G", is the characteristic relaxation time, alternatively referred to as "relaxation time" or $T_r$. Relaxation times of the Series A to F compositions are shown in the ternary plots of FIGS. 2 to 7; relaxation times are reported in units of milliseconds (ms).

Figure 2:
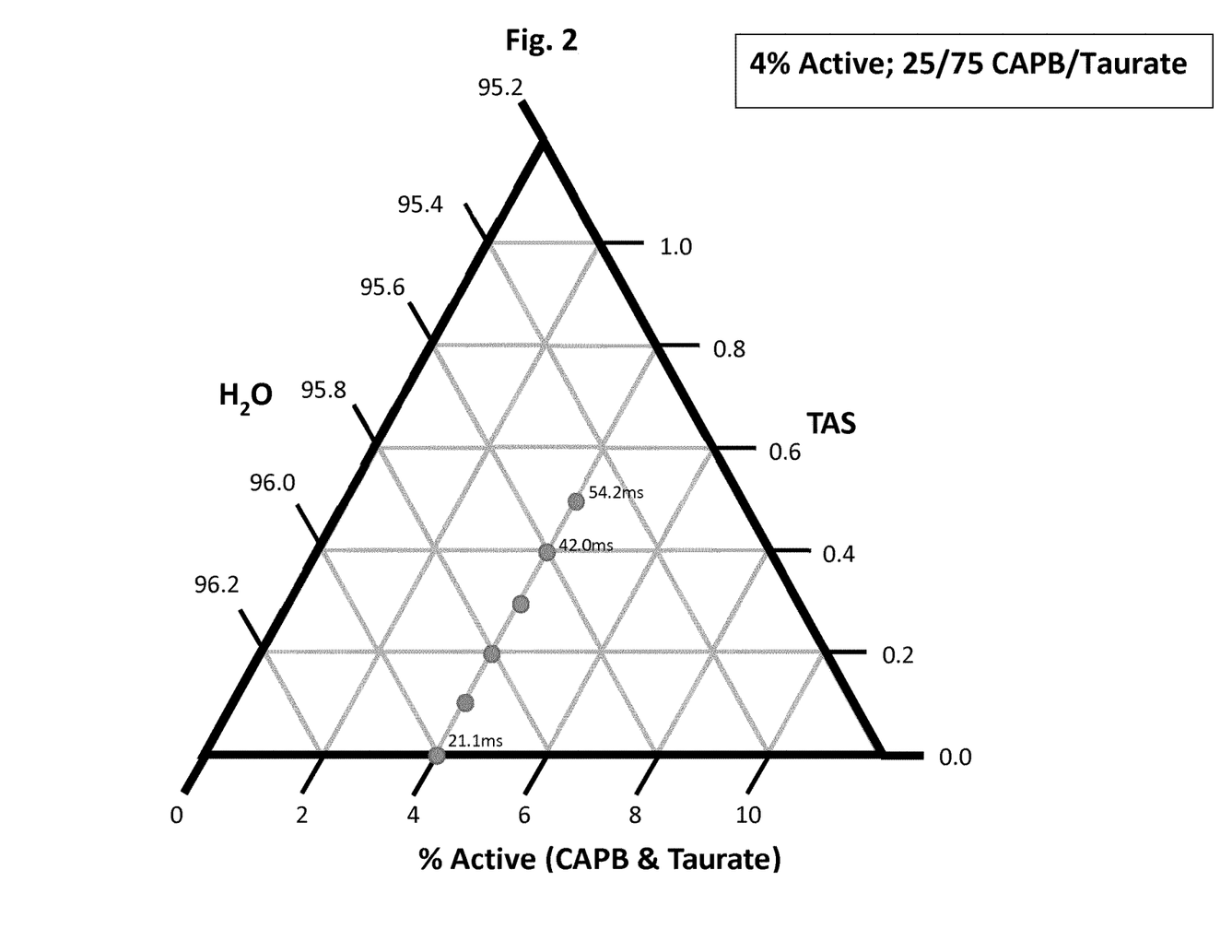
FIGS. 2 to 7 are ternary plots of relaxation times ($T_r$) for compositions containing a taurate surfactant, a betaine surfactant, and various levels of stearamidopropyl dimethylamine; the plots were derived from dynamic oscillatory measurements made under conditions as hereinafter described using a TA ARES-G2 rheometer configured as described below.

FIG. 2 is a plot of relaxation times of the Sample A series of compositions. The plotted relaxation times were very short and ranged from 21.1 ms to 54.2 ms; no crossover frequency was observed for the compositions containing 0.1 to 0.3 wt. % stearamidopropyl dimethylamine, an indication that these compositions did not build sufficient micellar structure to provide a measurable relaxation time.

Figure 3:
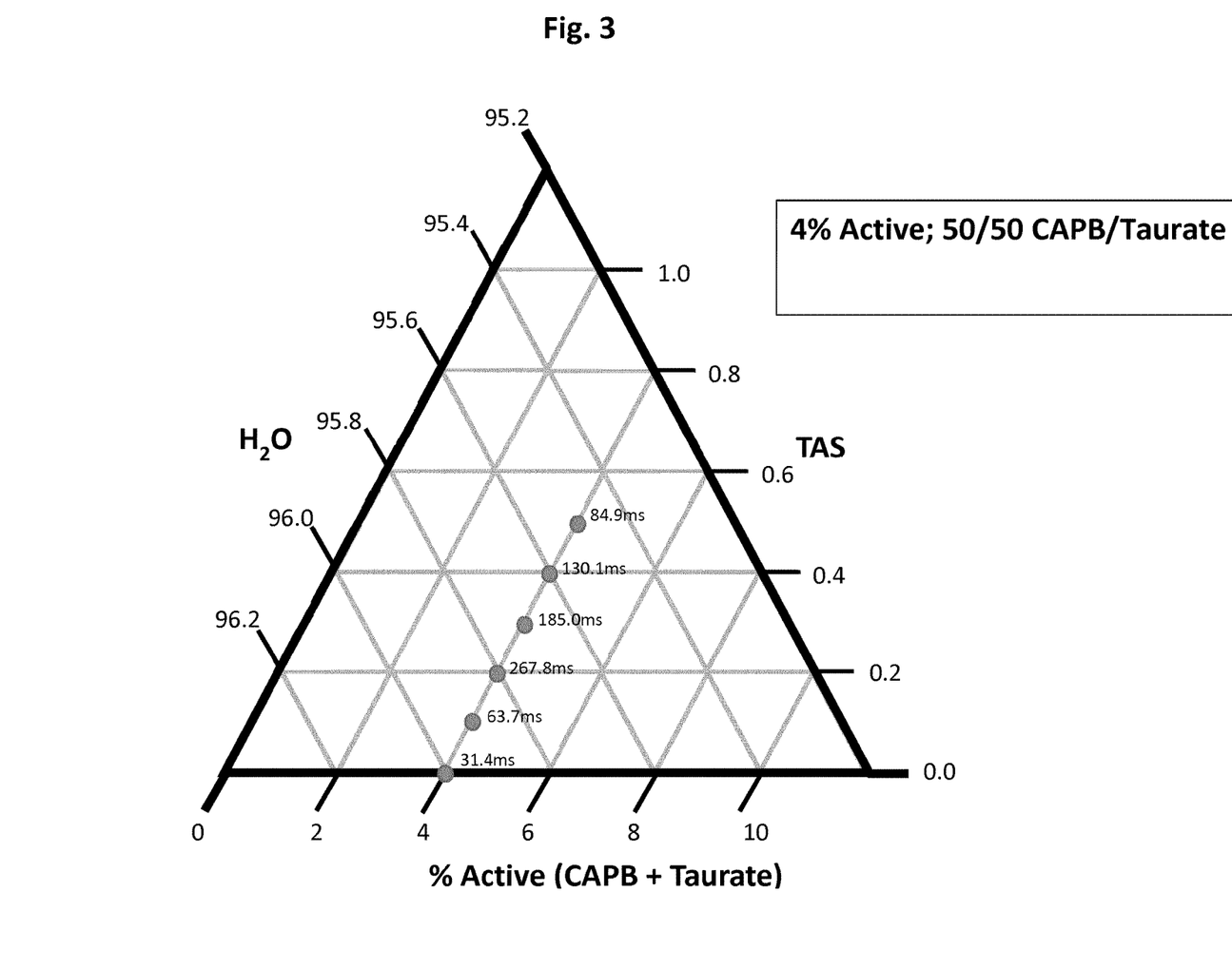

FIG. 3 is a plot of relaxation times of the Sample B series of compositions. The plotted relaxation times ranged from 31.4 ms to 267.8 ms. Relaxation times were shown to increase from 31.4 ms for the composition with no stearamidopropyl dimethylamine to 267.8 ms for the composition containing 0.2 wt. % stearamidopropyl dimethyl amine. Between 0.3 and 0.5 wt % stearamidopropyl dimethylamine relaxation times decreased from 185.0 ms to 84.9 ms, but were still significantly higher than the relaxation time for composition with no stearamidopropyl dimethylamine.

Figure 4:
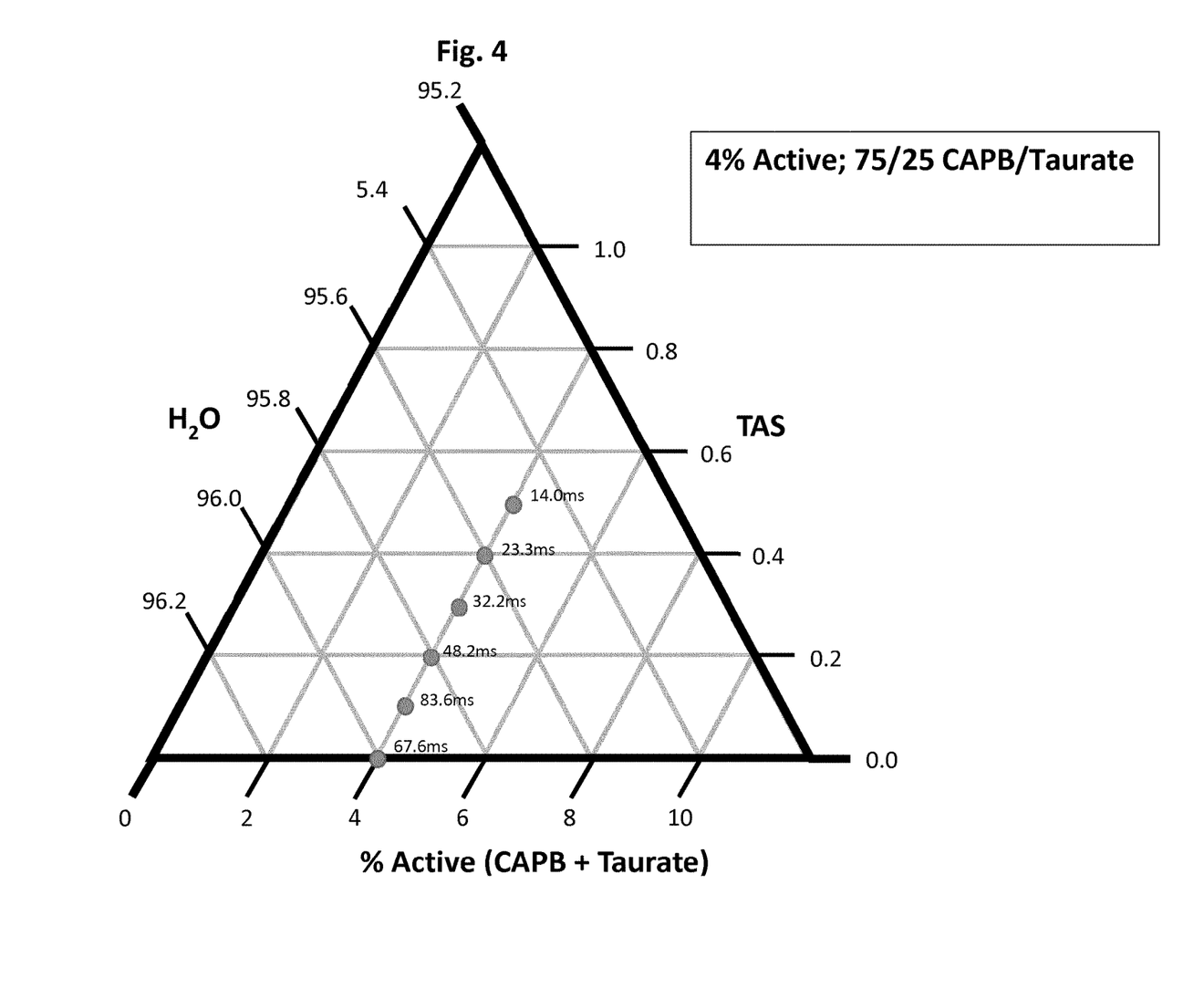

FIG. 4 is a plot of relaxation times of the Sample C series of compositions. Relaxation times were shown to increase from 67.6 ms for the composition with no stearamidopropyl dimethylamine to 83.6 ms for the composition containing 0.1 wt. % stearamidopropyl dimethylamine. Between 0.2 to 0.5 wt. % stearamidopropyl amine, the relaxation times decreased from 48.2 ms to 14.0 ms. The reported relaxation times are generally consistent with compositions that have a relatively weak micellar structure.

Figure 5:
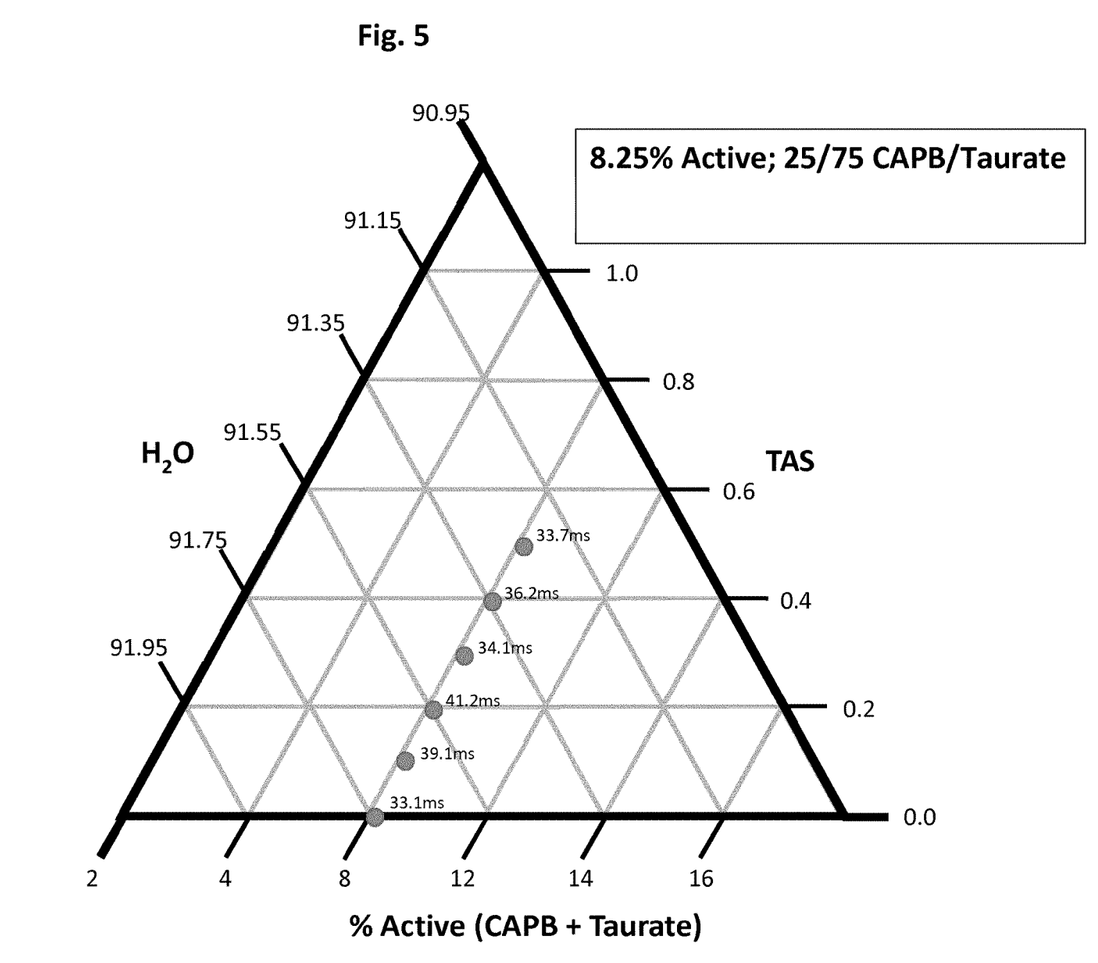

FIG. 5 is a plot of relaxation times of the Sample D series of compositions. The plotted relaxation times were relatively short and ranged from 33.1 ms to 41.2 ms. The reported relaxation times are generally consistent with compositions that have a relatively weak micellar structure.

Figure 6:
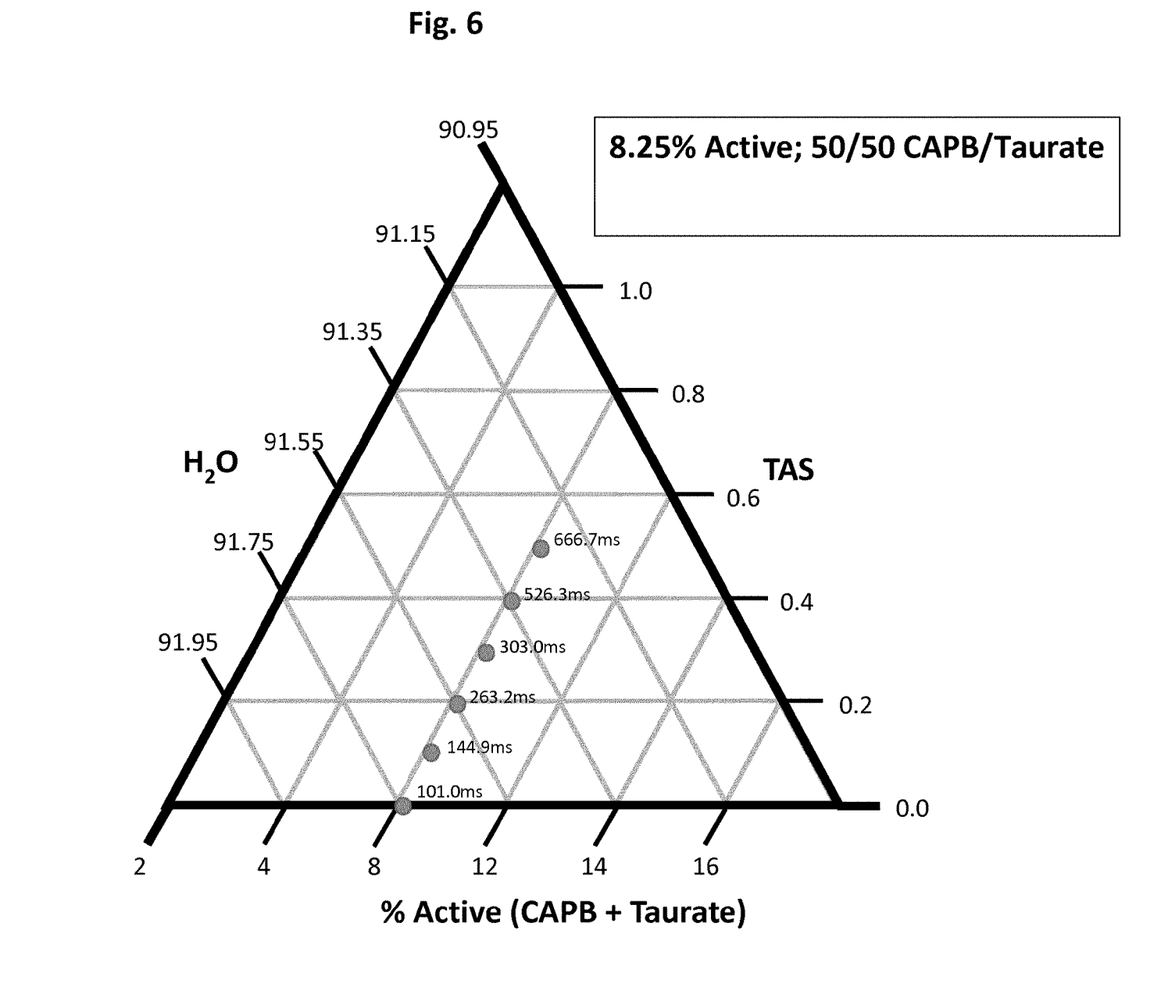

FIG. 6 is a plot of relaxation times of the Sample E series of compositions. The plotted relaxation times ranged from 101.0 ms to 666.7 ms. Relaxation times were shown to increase as the level of stearamidopropyl dimethylamine increased.

Figure 7:
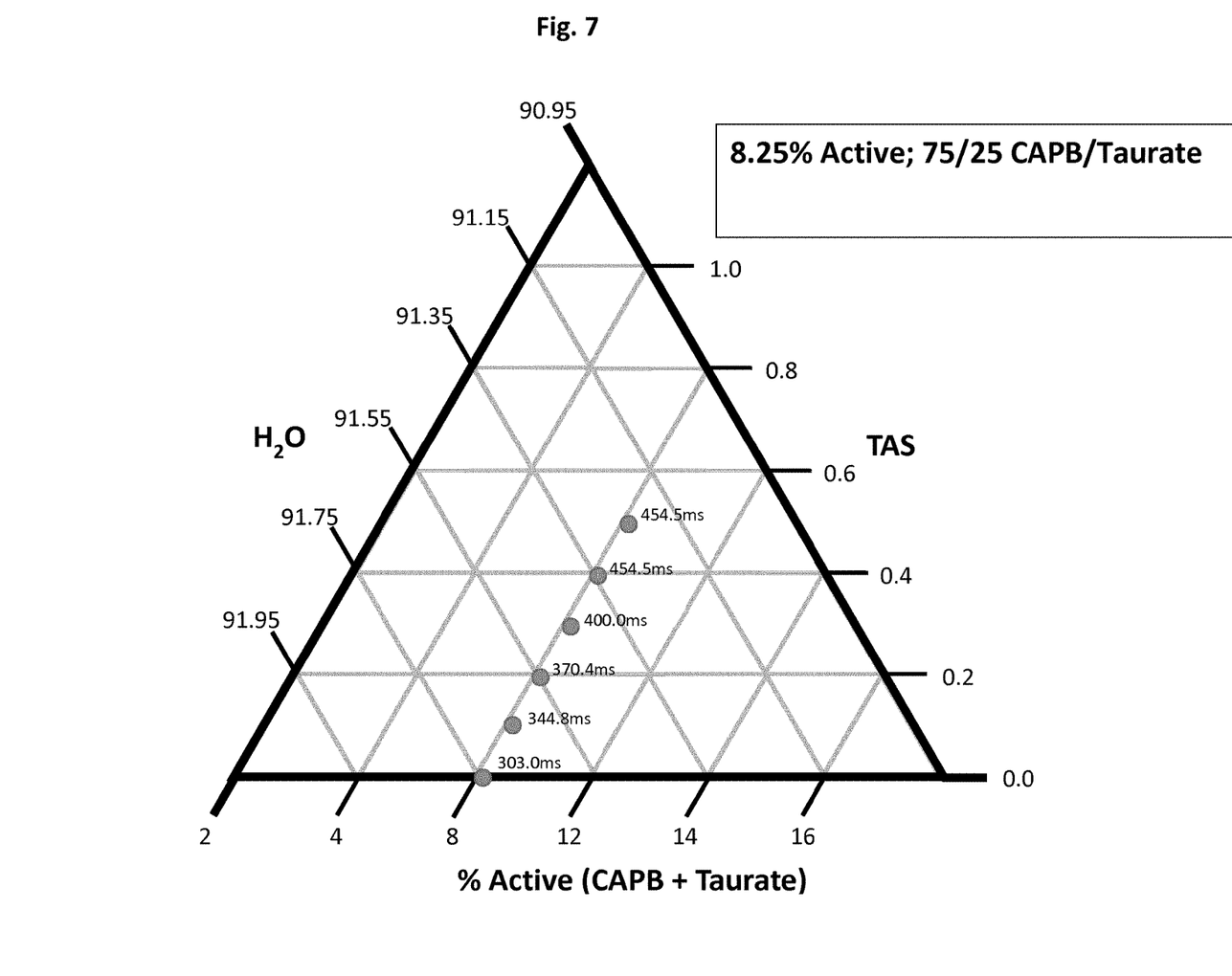

FIG. 7 is a plot of relaxation times of the Sample F series of compositions. The plotted relaxation times ranged from 303.0 ms to 454.5 ms, with relaxation times increasing as the level of stearamidopropyl dimethylamine increased to 0.4 wt. % of the composition. The relaxation time of the compositions containing 0.4 wt. % stearamidopropyl dimethylamine and the composition containing 0.5 wt. % stearamidopropyl dimethyl amine was essentially the same.

The plots of FIGS. 2 to 7 show that both the cleansing surfactant content and the amount of betaine surfactant relative to taurate surfactant to betaine surfactant can significantly impact the ability of stearamidopropyl dimethylamine to assist in building micellar structure.

Example 2

Compositions as described in Table 2A were prepared following the general procedure prepared above. The pH of the compositions ranged from 4.0 to 4.7. The initial viscosity of each of the resulting compositions was measured. Viscosity adjusting agent was post-added to the initially formed TAS-containing compositions, as indicated; sodium chloride to adjust the viscosity upward, or PPG-9 to adjust the viscosity downward. Viscosity adjusting agent was post-added until an adjusted viscosity within a target viscosity of 4000 to 8000 cP was obtained or the added amount of viscosity adjusting agent reached the maximum total amount. Viscosity adjusting agent was posted added in increments of 0.05 wt. % up to a total amount of 0.2 wt. %, and thereafter as increments of 0.1 wt. %, up to the maximum total amount of 2.0 wt. %, based on the total weight of the initially formed composition. Sodium chloride was post-added to the TAS-free C1 and C2 compositions in increments of 0.2, 0.3 and 0.5 wt. %, up to a total amount of 1.0 wt %, based on the total weight of the initially formed composition. At total post added salt levels of 0.2 wt %, 0.5. wt. % and 1.0 wt. %, the adjusted viscosity of the C1 composition was 2656 cP, 2508 cP, and 2706 cP, respectively. At total post-added salt levels of 0.2 wt %, 0.5. wt. % and 1.0 wt. %, the adjusted viscosities of the C2 composition were 6197 cP, 6443 cPs, and 7093 cP, respectively. Viscosity measurements were obtained using an AR2000EX rheometer from TA Instruments (30° C., 1 mm gap, 90 sec equilibrium time, 30 sec measurement, A-4 1/s, 40 mm steel plate spindle).

TABLE 2A

| Ingredient wt. % | Sample | | | | | |
|---|---|---|---|---|---|---|
| | C1 | C2 | C3 | C4 | C5 | C 6 |
| Initial Aliquot Water | To 100 | To 100 | To 100 | To 100 | To 100 | To 100 |
| Additional Water | 12 | 12 | 12 | 12 | 12 | 12 |
| Polyquaternium-10 | 0.2 | 0.2 | 0.2 | 0.2 | 0.2 | 0.2 |
| Tego ® Betain CK KB5* | 20.63 | 31.25 | 3.33 | 6.66 | 10.0 | 6.87 |
| Pureact WS Conc. | 6.87 | 10.41 | 10.0 | 6.66 | 3.333 | 20.63 |
| Stearamidopropyl dimethyl amine (TAS) | — | — | 0.10 | 0.10 | 0.10 | 0.10 |
| Fragrance | 0.7 | 0.9 | 0.9 | 0.9 | 0.9 | 0.9 |
| Disodium EDTA | 0.05 | 0.05 | 0.05 | 0.05 | 0.05 | 0.05 |
| Sodium Benzoate | 0.41 | 0.34 | 0.45 | 0.47 | 0.45 | 0.47 |
| Citric Acid (50 wt % Aqueous Solution) | 1.2 | 1.2 | 1.2 | 1.2 | 1.2 | 1.2 |
| Total Cleansing Surfactant (wt. %) | 8.25 | 12.5 | 4 | 4 | 4 | 8.25 |
| Weight Ratio Betaine:Taurate | 75:25 | 75:25 | 25:75 | 50:50 | 75:25 | 25:75 |
| Initial Viscosity (cP) | 3240 | 6128 | 3 | 339 | 691 | 59 |
| Hazy (Yes/No) | No | Yes | No | No | No | No |
| Viscosity adjusting agent (wt. %) | NaCl (1.0) | NaCl (1.0) | NaCl (2.0) | NaCl (2.0) | NaCl (2.0) | NaCl (2.0) |
| Adjusted Viscosity (cP) | 2706 | 7093 | 238 | 180 | 176 | 638 |
| Hazy (Yes/No) | Yes | Yes | Yes | Yes | Yes | Yes |

| Ingredient wt. % | Sample | | | | | |
|---|---|---|---|---|---|---|
| | 1 | 2 | 3 | 4 | 5 | 6 |
| Initial Aliquot Water | To 100 | To 100 | To 100 | To 100 | To 100 | To 100 |
| Additional Water | 12 | 12 | 12 | 12 | 12 | 12 |
| Polyquaternium-10 | 0.2 | 0.2 | 0.2 | 0.2 | 0.2 | 0.2 |
| Tego ® Betain CK KB5* | 13.75 | 13.75 | 20.63 | 31.25 | 20.83 | 10.41 |
| Pureact WS Conc. | 13.75 | 13.75 | 6.87 | 10.41 | 20.83 | 31.25 |
| Stearamidopropyl dimethyl amine (TAS) | 0.10 | 0.10 | 0.10 | 0.10 | 0.10 | 0.10 |
| Fragrance | 0.9 | 0.9 | 0.9 | 0.9 | 0.9 | 0.9 |
| Disodium EDTA | 0.05 | 0.05 | 0.05 | 0.05 | 0.05 | 0.05 |
| Sodium Benzoate | 0.43 | 0.43 | 0.40 | 0.34 | 0.40 | 0.45 |
| Citric Acid (50 wt % aqueous solution) | 1.2 | 1.2 | 1.2 | 1.2 | 1.2 | 1.2 |
| Total Cleansing Surfactant (wt. %) | 8.25 | 8.25 | 8.25 | 12.5 | 12.5 | 12.5 |
| Weight Ratio Betaine:Taurate | 50:50 | 50:50 | 75:25 | 75:25 | 50:50 | 25:75 |
| Initial Viscosity (cP) | 2327 | 2580 | 4741 | 10280 | 13990 | 259 |
| Hazy (Yes/No) | No | No | No | Yes | Yes | Yes |
| Viscosity adjusting agent (wt. %) | NaCl (0.7) | NaCl (0.7) | — | PPG-9 (0.1) | PPG-9 (0.15) | NaCl (2.0) |
| Adjusted Viscosity (cP) | 4683 | 4876 | — | 6210 | 6704 | 4765 |
| Hazy (Yes/No) | Yes | Yes | — | Yes | Yes | Yes |

*Tego Betain CK KB5 from Evonik Industries; ≈30% cocamidopropyl betaine
**Pureact WS Conc. from Innospec Performance Chemicals; ≈30% sodium methyl cocoyl taurate Samples 1 to 6 and comparative samples C3 to C6 all contained 0.1 wt. % stearamidopropyl dimethyl amine. The initial viscosities of samples 4 and 5 (cleansing surfactant content of 12.5 wt. %; betaine:taurate weight ratio of 75:25 and 50:50, respectively) were above the targeted range and had to be adjusted downward. The viscosity of sample 6 (cleansing surfactant content of 12.5 wt. %; betaine:taurate weight ratio of 25:75) was brought within the targeted range by the addition of 2.0 wt. % sodium chloride. The C6 sample (cleansing surfactant content of 8.25 wt. %; betaine:taurate weight ratio of 25:75) was not brought with the targeted ange by the addition of sodium chloride at the highest level considered (2.0 wt. %). The initial viscosity of sample 3 was within the targeted viscosity range and did not require viscosity adjustment.

The viscosities of comparative samples C3, C4 and C5 (total surfactant content of 4 wt. %; betaine:taurate ratios of 25:75, 50:50 and 75:25, respectively) was not brought within the targeted range by the addition of sodium chloride at highest level considered (2.0 wt. %). The viscosities of samples 1 and 2 (cleansing surfactant content of 8.25 wt. % betaine:taurate sodium ratio of 50:50) were brought within the targeted range by the addition of 0.7 wt. % sodium chloride. The initial viscosity of sample 3 (cleansing surfactant content of 8.25 wt. %, betaine:taurate ratio of 75:25) was within the targeted range and did not require adjustment.

The C1 sample had a significantly lower initial viscosity (3240 cPs) than sample 3 (initial viscosity 4741 cP), which, pre-salt adjustment, contained a like amount of cleansing surfactant (8.25%) and a like betaine:taurate ratio (75:25); the inclusion of TAS in sample 3 being shown to develop composition viscosity. Salt addition did not bring the adjusted viscosity of the C1 sample within the targeted range; at 1.0 wt. % of added salt, the adjusted viscosity of the C1 composition was less than the initial viscosity. The C2 sample had a significantly lower initial viscosity (6128 cP) than sample 4 (initial viscosity 10280 cP), which contained a like amount of cleansing surfactant and a like betaine:taurate ratio (75:25); the inclusion of TAS in sample 4 being shown to develop composition viscosity.

Foam properties of sample 3 and the viscosity adjusted compositions of samples 1 to 2, 4 to 6 and C3 to C6 are reported in Table 2B. Foam properties were obtained by the following general procedures.

Foam volume measurements were obtained using a Sitafoam R-2000 Foam Tester from SITA Lab Solutions (Sita Foam Software D/DAC; version 1.0.11.549). The water reservoir of the tester was filled with water at a temperature of 40-42° C. Test settings were adjusted to 40 stir cycles, 20 seconds per cycle, at 1000 rpm with 250 ml water. A 1 g sample of the composition to be tested was introduced to the tester, and the foam volume measured under the settings described. The volume of foam generated by the sample is reported in ml.

Foam density and stability were measured by the following procedure:
Tare a 100 m graduated cylinder on a balance.
Into a Braun kitchen blender, measure 200 ml of tap water at 45° C. and add 2 ml of the composition to be tested.
Using a timer, use the "pulse" switch for 10s and release the switch without stopping the timer, pausing pulsing for 10 seconds.
Repeat the 10 second pulse/10 second pause cycles until 70 seconds are elapsed (a total of three and a half cycles).
Transfer the resulting foam ton the graduated cylinder until the level reaches the 100 ml mark.
Record the weight of the foam as shown on the balance (density).
Start the timer for 5 minutes and record the volume of liquid at the bottom of the graduated cylinder (stability)

TABLE 2B

| Sample | Foam Vol. (ml) | Foam Density (g/100 ml) | Foam Stability (ml) |
| --- | --- | --- | --- |
| 1 | 427 | 8.7 | 6.5 |
| 2 | 411 | 8.1 | 8.0 |
| 3 | 450 | 15.0 | 13.0 |
| 4 | 446 | 8.7 | 7.5 |
| 5 | 441 | 9.5 | 8.0 |
| 6 | 424 | 10.3 | 9.0 |
| C3 | 391 | 8.08 | 6.5 |
| C4 | 399 | 9.92 | 7.0 |
| C5 | 321 | 11.82 | 9.0 |
| C6 | 409 | 9.97 | 8.0 |

On balance, all samples tested had acceptable foam properties, with samples 3 to 5 providing the highest foam volumes.

Salon testing (50 trained panelists) was carried out on the sample 3 composition. In such testing, the sample 3 composition was perceived as having good cleansing properties.

Example 3

Compositions as described in Tables 3 and 4 below were prepared by means of the following procedure, a variation of the general procedure described above.

Reserve approximately 10 to 15% of the initial water. Add polyquaternium-10 to the remainder of the initial water, and begin heating to a target temperature of 60° C. to 65° C. (70° C. if stearamidopropyl dimethylamine is to be added). Once the polyquaternium-10 is fully dissolved, add the sodium cocoyltaurate (Pureact WS Conc.) and mix until dissolved; if used, add stearamidopropyl dimethylamine and mix until dissolved. Begin cooling to 30° C. During the cooling phase, add the cocamidopropyl betaine (Tego® Betain CK KB5) and mix until dissolved. Add the disodium EDTA and sodium benzoate, pre-dispersed in the reserved water (warmed to 40-60° C.). When the mixture has cooled to below 35° C., add fragrance and adjust to a pH of 4.2-4.8 by the addition of citric acid, then add the sodium chloride as indicated. Viscosities of the resulting compositions were measured using a discovery hybrid rheometer (model DHR-2) from TA Instruments (30° C. at 4 reciprocal seconds, sandblasted plate). Composition viscosities are reported in Table 4 below.

Light transmission through the compositions was measured using a Formulaction Turbiscan LAB, which uses a Static Multiple Light Scattering method. A ΔT of >−20% (compared against a sample of distilled water) is herein considered to be "transparent".

TABLE 3

| Ingredient wt. % | General Formulation of Table 4 Samples |
| --- | --- |
| Initial Water (deionized) | To 100 |
| Polyquaternium- 10 | 0.2 |
| Pureact WS Conc.** | As indicated in Table 4 |
| Stearamidopropyl dimethyl amine | As indicated in Table 4 |
| Tego ® Betain CK KB5* | As indicated in Table 4 |
| Disodium EDTA | 0.05 |
| Sodium Benzoate | 0.5 |
| Fragrance | 0.7 |
| Citric Acid (50 wt. % aq. solution) | 1.2 |
| Sodium Chloride | As indicated in Table 4 |

*Tego ®Betain CK KB5 from Evonik Industries; ≈30% cocamidopropyl betaine
**Pureact WS Conc. from Innospec Performance Chemicals; ≈30% sodium methyl cocoyl taurate

TABLE 4

| | Sample | | | | | | | | | |
| --- | --- | --- | --- | --- | --- | --- | --- | --- | --- | --- |
| | A(1) | A(2) | A(3) | A(4) | A(5) | B(1) | B(2) | B(3) | B(4) | B(5) |
| Pureact WS Conc. (wt %) | 6.66 | 6.66 | 6.66 | 6.66 | 6.66 | 6.66 | 6.66 | 6.66 | 6.66 | 6.66 |

TABLE 4-continued

| | | | | | | | | | | |
|---|---|---|---|---|---|---|---|---|---|---|
| Stearamidopropyl dimethyl amine (wt %) | — | — | — | — | — | 0.3 | 0.3 | 0.3 | 0.3 | 0.3 |
| Tego ® Betain CK KB5 (wt %) | 6.66 | 6.66 | 6.66 | 6.66 | 6.66 | 6.66 | 6.66 | 6.66 | 6.66 | 6.66 |
| Sodium Chloride | — | 0.5 | 1 | 1.5 | 2 | — | 0.5 | 1 | 1.5 | 2 |
| Total Cleansing Surfactant (wt. %) | 4 | 4 | 4 | 4 | 4 | 4 | 4 | 4 | 4 | 4 |
| Weight Ratio Betaine:Taurate | 50:50 | 50:50 | 50:50 | 50:50 | 50:50 | 50:50 | 50:50 | 50:50 | 50:50 | 50:50 |
| Viscosity (cP) | 51 | 120 | 310 | 501 | 581 | 676 | 588 | 181 | 136 | 114 |
| ΔT (%) | −5.34 | −2.07 | −3.83 | −74.46 | −82.84 | −2.96 | −2.53 | −85.63 | −86.84 | −86.76 |

| | E(1) | E(2) | E(3) | E(4) | E(5) | F(1) | F(2) | F(3) | F(4) | F(5) |
|---|---|---|---|---|---|---|---|---|---|---|
| Pureact WS Conc. (wt %) | 9.99 | 9.99 | 9.99 | 9.99 | 9.99 | 9.99 | 9.99 | 9.99 | 9.99 | 9.99 |
| Stearamidopropyl dimethyl amine (wt %) | — | — | — | — | — | 0.15 | 0.15 | 0.15 | 0.15 | 0.15 |
| Tego ® Betain CK KB5 (wt %) | 9.99 | 9.99 | 9.99 | 9.99 | 9.99 | 9.99 | 9.99 | 9.99 | 9.99 | 9.99 |
| Sodium Chloride | — | 0.5 | 1 | 1.5 | 2 | — | 0.5 | 1 | 1.5 | 2 |
| Total Cleansing Surfactant (wt. %) | 6 | 6 | 6 | 6 | 6 | 6 | 6 | 6 | 6 | 6 |
| Weight Ratio Betaine:Taurate | 50:50 | 50:50 | 50:50 | 50:50 | 50:50 | 50:50 | 50:50 | 50:50 | 50:50 | 50:50 |
| Viscosity (cP) | 114 | 299 | 651 | 1129 | 1802 | 222 | 553 | 1144 | 1872 | 2626 |
| ΔT (%) | — | — | — | — | — | — | — | — | — | — |

| | Sample | | | | | | | | | |
|---|---|---|---|---|---|---|---|---|---|---|
| | I(1) | I(2) | I(3) | I(4) | I(5) | J(1) | J(2) | J(3) | J(4) | J(5) |
| Pur eact WS Conc. (wt %) | 6.66 | 6.66 | 6.66 | 6.66 | 6.66 | 20 | 20 | 20 | 20 | 20 |
| Stearamidopropyl dimethyl amine (wt %) | — | — | — | — | — | 0.3 | 0.3 | 0.3 | 0.3 | 0.3 |
| Tego ® Betain CK KB5 (wt %) | 20 | 20 | 20 | 20 | 20 | 6.66 | 6.66 | 6.66 | 6.66 | 6.66 |
| Sodium Chloride | — | 0.5 | 1 | 1.5 | 2 | — | 0.5 | 1 | 1.5 | 2 |
| Total Cleansing Surfactant (wt. %) | 8 | 8 | 8 | 8 | 8 | 8 | 8 | 8 | 8 | 8 |
| Weight Ratio Betaine:Taurate | 75:25 | 75:25 | 75:25 | 75:25 | 75:25 | 25:75 | 25:75 | 25:75 | 25:75 | 25:75 |
| Viscosity (cP) | 1084 | 1292 | 1386 | 1615 | 1858 | 1304 | 1526 | 1747 | 2145 | 2057 |
| ΔT (%) | −4.60 | −85.86 | −85.14 | −85.96 | −86.10 | −2.83 | −86.61 | −86.84 | −86.87 | −86.90 |

| | M(1) | M(2) | M(3) | M(4) | M(5) | S(1) | S(2) | S(3) | S(4) | S(5) |
|---|---|---|---|---|---|---|---|---|---|---|
| Pureact WS Conc. (wt %) | 13.33 | 13.33 | 13.33 | 13.33 | 13.33 | 20 | 20 | 20 | 20 | 20 |
| Stearamidopropyl dimethyl amine (wt %) | 0.15 | 0.15 | 0.15 | 0.15 | 0.15 | — | — | — | — | — |
| Tego ® Betain CK KB5 (wt %) | 13.33 | 13.33 | 13.33 | 13.33 | 13.33 | 6.66 | 6.66 | 6.66 | 6.66 | 6.66 |
| Sodium Chloride | — | 0.5 | 1 | 1.5 | 2 | — | 0.5 | 1 | 1.5 | 2 |
| Total Cleansing Surfactant (wt. %) | 8 | 8 | 8 | 8 | 8 | 8 | 8 | 8 | 8 | 8 |
| Weight Ratio Betaine:Taurate | 50:50 | 50:50 | 50:50 | 50:50 | 50:50 | 25:75 | 25:75 | 25:75 | 25:75 | 25:75 |
| Viscosity (cP) | 1069 | 2416 | 3978 | 5125 | 5671 | 12 | 19 | 41 | 79 | 248 |
| ΔT (%) | −2.56 | −15.37 | −86.55 | −86.87 | −86.90 | −3.37 | −3.14 | −6.19 | −81.82 | −84.47 |

| | Sample | | | | | | | | | |
|---|---|---|---|---|---|---|---|---|---|---|
| | T(1) | T(2) | T(3) | T(4) | T(5) | Y(1) | Y(2) | Y(3) | Y(4) | Y(5) |
| Pureact WS Conc. (wt %) | 20 | 20 | 20 | 20 | 20 | 20 | 20 | 20 | 20 | 20 |
| Stearamidopropyl dimethyl amine (wt %) | 0.3 | 0.3 | 0.3 | 0.3- | 0.3 | — | — | — | — | — |
| Tego ® Betain CK KB5 (wt %) | 6.66 | 6.66 | 6.66 | 6.66 | 6.66 | 20 | 20 | 20 | 20 | 20 |
| Sodium Chloride | — | 0.5 | 1 | 1.5 | 2 | — | 0.5 | 1 | 1.5 | 2 |
| Total Cleansing Surfactant (wt. %) | 8 | 8 | 8 | 8 | 8 | 12 | 12 | 12 | 12 | 12 |

TABLE 4-continued

| Weight Ratio Betaine:Taurate | 25:75 | 25:75 | 25:75 | 25:75 | 25:75 | 50:50 | 50:50 | 50:50 | 50:50 | 50:50 |
|---|---|---|---|---|---|---|---|---|---|---|
| Viscosity (cP) | 39 | 94 | 231 | 495 | 1245 | 11168 | 16161 | 19251 | 22904 | 23074 |
| ΔT (%) | −3.41 | −3.96 | −75.06 | −84.66 | −86.18 | −86.56 | −86.68 | −86.89 | −86.96 | −87.03 |

| | Z(1) | Z(2) | Z(3) | Z(4) | Z(5) |
|---|---|---|---|---|---|
| Pureact WS Conc. (wt %) | 20 | 20 | 20 | 20 | 20 |
| Stearamidopropyl dimethyl amine (wt %) | 0.3 | 0.3 | 0.3 | 0.3 | 0.3 |
| Tego ® Betain CK KB5 (wt %) | 20 | 20 | 20 | 20 | 20 |
| Sodium Chloride | — | 0.5 | 1 | 1.5 | 2 |
| Total Cleansing Surfactant (wt. %) | 12 | 12 | 12 | 12 | 12 |
| Weight Ratio Betaine:Taurate | 50:50 | 50:50 | 50:50 | 50:50 | 50:50 |
| Viscosity (cP) | 17632 | 23055 | 24150 | 26050 | 25917 |
| ΔT (%) | −86.84 | −86.90 | −86.96 | −86.95 | −86.92 |

What is claimed is:

1. A personal cleansing composition comprising:
   a) an amidoamine surfactant of the formula:

$$R^5R^6N-(CH_2)_x-NHC(O)R^7 \qquad (I)$$

wherein $R^5$ and $R^6$ are independently methyl or ethyl, x is 2 or 3, and $R^7$ is C6 to C30 alkyl, wherein $R^7$ is saturated or unsaturated,
   b) 5 to 15 wt. % cleansing surfactant,
   c) water, and
   d) protonating agent
   wherein:
   the cleansing surfactant comprises from 85 to 100% by weight of a combination of betaine surfactant and taurate surfactant, and wherein:
   when the composition comprises 5 to 6 weight percent of cleansing surfactant, the weight ratio of betaine surfactant to taurate surfactant is from 55:45 to 45:55;
   when composition comprises from greater than 6 weight percent to up to 10 weight percent of cleansing surfactant, the weight ratio of betaine surfactant to taurate surfactant is from 80:20: to 40:60; and
   when the composition comprises greater than 10 weight percent of cleansing surfactant, the weight ratio of betaine surfactant to taurate surfactant is from 80:20: to 20:80;
   wherein the composition is essentially free of sulfate surfactant.

2. The personal cleansing composition according to claim 1, wherein the amidoamine surfactant is present in an amount of up to 2 wt. %, based on the total weight of the composition.

3. The personal cleansing composition according to claim 1, wherein the composition comprises from 0.05 to 1 wt. % of the amidoamine surfactant, based on the total weight of the composition.

4. The personal cleansing composition according to claim 1, wherein the betaine surfactant is an amidobetaine and the taurate surfactant is an acyl taurate.

5. The personal cleansing composition according to claim 1, wherein the taurate surfactant comprises sodium methyl cocoyl taurate and the betaine surfactant comprises cocamidopropyl betaine.

6. The personal cleansing composition according to claim 1, wherein the composition comprises from 6 to 12 wt. % of cleansing surfactant, based on the total weight of the composition.

7. The personal cleansing composition according to claim 1, wherein the composition has an isotropic surfactant phase.

8. The composition according to claim 1, wherein the amidoamine surfactant comprises stearamidopropyl dimethyl amine.

9. The personal cleansing composition according to claim 1, that is transparent.

10. The personal cleansing composition according to claim 1 that is essentially free of (meth)acrylate polymers and copolymers.

11. The personal cleansing composition according to claim 1 that further comprises electrolyte.

12. A method of adjusting the viscosity of a composition, the method comprising the steps of:
    I) providing a composition according to claim 1: and
    II) adding electrolyte to the composition,
    wherein the addition of electrolyte increases the viscosity of the resulting composition.

13. The method according to claim 12 wherein the electrolyte is sodium chloride, ammonium chloride, magnesium chloride, sodium sulfate or sodium citrate.

14. The personal cleansing composition according to claim 1, wherein the amidoamine is selected from the group consisting of stearamidopropyldimethylamine, stearamidoethyldiethylamine, stearamidopropyldiethylamine, palmitoamidopropyldimethylamine, palmitamidopropyldiethylamine, palmitoamidoethyldimethylamine, behenamidopropyldimethylamine, behenamidoethyldimethylamine, and arachiamidopropyldimethylamine.

15. The personal cleansing composition according to claim 4, wherein the acyl taurate is of the formula:

$$R8C(O)N(R9)(CH2)ySO3M \qquad (IIa),$$

wherein R8 is C6 to C30 alkyl,
y is 2 or 3,
R9 is hydrogen or methyl, and
M is a solubilizing cation.

16. The personal cleansing composition according to claim 15, wherein y is 2.

17. The personal cleansing composition according to claim 15, wherein M is hydrogen, ammonium, alkali metal cation, a C1 to C4 alkanolammonium cation, or a basic amino acid cation.

18. The personal cleansing composition according to claim 1, wherein the betaine is represented by the general formula:

$$R10[C(O)NH-(CH2)y]z-N+(R11)(R12)CH2CO2 \qquad (III)$$

where R10 is C6 to C30, z is 0 or 1,

R11 and R12 are independently alkyl, hydroxyalkyl or carboxyalkyl of 1 to 3 carbon atoms, and y is 2 or 3; and salts thereof.

19. The personal cleansing composition according to claim 18, wherein R11 and R12 are methyl.

\* \* \* \* \*